United States Patent [19]

Pesque

[11] Patent Number: 4,853,904

[45] Date of Patent: Aug. 1, 1989

[54] APPARATUS FOR EXAMINING A MOVING OBJECT BY MEANS OF ULTRASOUND ECHOGRAPHY

[75] Inventor: Patrick R. A. Pesque, Perigny, France

[73] Assignee: U.S. Philips Corporation, New York, N.Y.

[21] Appl. No.: 97,224

[22] Filed: Sep. 15, 1987

[30] Foreign Application Priority Data

Sep. 19, 1986 [FR] France .................. 86 13140

[51] Int. Cl.$^4$ .......................................... G01S 15/58
[52] U.S. Cl. ............................ 367/89; 128/661.08; 73/597
[58] Field of Search ............ 367/89; 342/104, 105; 73/488, 490, 627, 597; 128/663, 661.08

[56] References Cited

U.S. PATENT DOCUMENTS 3,947,805 3/1976 Brown .................. 367/126
4,510,587 4/1985 Schneider .................. 367/89

OTHER PUBLICATIONS

Dotti et al., Blood Flow Measurements by Ultrasound Correlation Techniques, Nov. 1976, pp. 571–575.
Bassini et al., In Vivo Recording of Blood Velocity Profiles in Studies in Virtro of Profile Alterations Induced by Known Stenosis, 1982, pp. 185–194.
Bassini et al., Ultrasonic Noninvasive Blood Flow Meter Based on Cross Correlation Techniques, 1979, pp. 273–278.

Primary Examiner—Thomas H. Tarcza
Assistant Examiner—Daniel T. Pihulic
Attorney, Agent, or Firm—Jack E. Haken

[57] ABSTRACT

An apparatus for examining a moving object by means of ultrasound echography, enabling the measurement of the axial speed of said movement or the projection of the speed on the axis z of a beam of ultrasound excitations transmitted by an ultrasound transducer (10) with a repetition period T. The apparatus also comprises a transmission stage (20) and a stage (30) for receiving and processing the echographic signals returned to the transducer (10). The stage (30) for receiving and processing the echographic signals comprises a circuit (330) for estimating said axial speed $V_{iz}(t)$ which comprises a circuit (340) for extracting the time shift $\tau_i(t)$ between two consecutive echoes $e_i(t)$ and $e_{i+1}(t)$, constructed for solving the equation in $\tau_i(t)$:

$$e_{i+1}(t) = \sum_{n=0}^{p} \frac{(-1)^n}{n!} e_i^{(n)}(t) \cdot \tau_i^n(t)$$

where $e_i(t)$ is the derivative of the order "n" with respect to the time of the echo $e_i(t)$, and a circuit (350) for multiplication by $C/2T$ so as to obtain $V_{iz}(t)$ on the basis of $\tau_i(t)$, where C is the propagation speed of the ultrasound wave.

9 Claims, 3 Drawing Sheets

APPARATUS FOR EXAMINING A MOVING OBJECT BY MEANS OF ULTRASOUND ECHOGRAPHY

The invention relates to an apparatus for examining a moving object by means of ultrasound echography, enabling the measurements of the axial speed of said movement i.e. the projection of the speed on the axis "z" of a beam of ultrasound excitations which are periodically transmitted by at least one ultrasound transducer with a repetition period "T", which apparatus also comprises a transmission stage and a stage for receiving and processing the echographic signals returned to the transducer.

The invention can be very advantageously used for the echographic examination of moving organs, such as the heart, and blood flows.

The technical problem to be solved by any method and any apparatus for examining a moving object by means of ultrasound echography is that an exact as possible estimation must be made of the axial speed of the motion studied in order to obtain, using display devices, exact images of the organs and blood flows subjected to an ultrasound echographic examination.

For a number of years various solutions to this problem have been proposed, notably pulsed-wave ultrasound Doppler systems which are currently used for measuring the blood flow speeds in a given point, or at least the protection of such speeds on the axis of the beam transmitter by the ultrasound transducers. More recently, apparatus have become available which enable real-time determination of the distribution of the flow speeds along the path followed by the ultrasound wave and even across the sectional plane obtained by way of a scanning motion of the transducer. The majority of these systems utilize the frequency shift or the phase shift of the signal returned by the moving targets in order to derive the axial speed of the blood flows therefrom. For example, European patent application No. 0,092,841 relates to such an apparatus, which utilizes the measurement of the phase shift between the successive echoes returned by the moving targets in response to a recurrent excitation.

However, the apparatus for carrying out this known method utilizing the phase shift are restricted by an uncertainty relation which links the axial resolution $\Delta z$ and the precision of the measurement of the speed $\Delta V/V$ to the wavelength $\lambda$:

$$\frac{\Delta V}{V} \cdot \Delta z = \frac{\lambda}{2}$$

This relation, cited in Chapter II, section 2.3-a, of the publication "Doppler Ultrasound and Its Use in Clinical Measurement", P. ATKINSON and J. P. WOODCOCK, Academic Press, 1982, thus imposes a compromise between the axial resolution and the precision of the speed measurement; this is incompatible with the exact measurement of a speed profile or a blood flow image.

In this respect, French Patent Application No. 85 17 841 (discloses a different method of processing the echographic signal where the precision of the speed measurement is not limited by the spatial resolution. This is a time analysis method which consists in the interpretation of the returning of the ultrasound signals in terms of the shifting in time of the echographic signals after each transmission of pulse signals instead of in terms of frequency shift or phase shift. This method is based on the following principle: assume that an object moves at the axial speed $V_z(t)$ (the axial speed is the projection of the speed on the axis "z" of an ultrasound excitation beam transmitted by an ultrasound transducer with a repetition period "T"). If at the instant $t=0$, i.e. when the object is situated at a distance "z" from said transducer, the transducer transmits a first ultrasound excitation, the echo $e_1(t)$ returned by the object will be received at the instant $t_1 = 2z/C$, where C is the propagation speed of the ultrasound wave. Subsequently, if at the instant $t=T$ the transducer transmits a second ultrasound excitation the echo $e_2(t)$ returned by the moving object will be detected by the transducer at the instant $t=T+2[z+V_z(t)T]/C$; the object thus has travelled the distance $V_z(t)T$ during the period "T". When the time origin for the second echo is taken as the instant $t=T$ (origin of the corresponding excitation), the relation $e_2(t) = e_1[t - \tau(t)]$ is obtained, where $\tau(t) = 2V_z(t)T/C$. This relation is very general and can be written as:

$$e_{i+1}(t) = e_i[t - \tau_i(t)] \quad (1)$$

$$\tau_i(t) = 2V_{iz}(t)T/C \quad (2)$$

$\tau_i(t)$ thus being the time shift induced by the displacement of the object between the excitations "i" and "i+1".

Thus, it appears from the formule (2) that the axial speed $V_{iz}(t)$ can be measured on the basis of the time shift $\tau_i(t)$ which is extracted from the formule (1) by appropriate processing.

French Patent Application No. 85 17 851 proposes an extraction method for the time shift $\tau_i(t)$ which utilizes the intercorrelation functions, the desired time shift being that for which the intercorrelation function between two successive echoes $e_i(t)$ and $e_{i+1}(t)$ is maximum. Even though this method offers the advantage of providing an exact axial speed $V_{iz}(t)$, it has the drawback that it necessitates the use of a complex device for performing the method, which device includes not only a transmission stage and a receiving and processing stage for the echographic signals returned to the transducer, but also numerous correlation circuits, as many averaging circuits and an interpolation circuit in the form of a microprocessor or wired logic.

The general technical problem to be solved in accordance with the invention is an apparatus for examining an object by ultrasound echography which achieves exact measurement of the axial speed without restrictions due to the axial resolution as well as ease of execution by means of simple electronic circuits. In a specific embodiment in accordance with the invention for blood flows, it is found that the signal returned by the blood is very weak in comparison with the fixed echoes. The proposed apparatus should, therefore, enable the extraction of the desired signal, in spite of the presence of these parasitic fixed echoes.

To achieve this, the apparatus in accordance with the invention is characterized in that said stage for receiving and processing the echographic signals comprises a circuit for estimating said axial speed $V_{iz}(t)$ which comprises on the one hand a circuit for extracting the time shift $\tau_i(t)$ between two successive echoes $e_i(t)$ and $e_{i+1}(t)$ which is constructed so as to solve the equation in $\tau_i(t)$:

$$e_{i+1}(t) = \sum_{n=0}^{p} \frac{(-1)^n}{n!} e_1^{(n)}(t) \cdot \tau_i^{n}(t) \quad (3)$$

where $e_i^{(n)}(t)$ is the derivative of the order "n" with respect to the time of the echo $e_i(t)$ and, on the other hand, a circuit for multiplication by $C/2T$ in order to obtain $V_{iz}(t)$ on the basis of $\tau_i(t)$, C being the propagation speed of the ultrasound wave.

By way of example said development limited to the order 1 is performed, the time shift $\tau_i(t)$ then being given by:

$$\tau_i(t) = [e_i(t) - e_{i+1}(t)]/e_i^{(1)}(t) \quad (4).$$

With respect to this formule it is to be noted that the sign of $\tau_i(t)$ and hence the sign of $V_{iz}(t)$ can thus be determined, so that the direction of the axial speed can be obtained. Actually a negative time shift represents a motion towards the transducer, whilst a positive shift is characteristic of a motion away from the transducer. The method relating to the use of the formule (4) can be executed in a substantially simplified form by means of a device such as said extraction circuit for the time shift $\tau_i(t)$ which comprises a delay line, a subtractor, a circuit for calculating first derivatives with respect to time, and a divider. In addition to its simplicity, this device also offers the advantage of having a completely analog construction.

In the specific embodiment for blood flows, the circuit for eliminating the fixed echoes and for attenuating the echoes relating to slow motions, comprising a subtractor for two consecutive echographic lines. The signal resulting from this difference is subsequently processed by the circuit for estimating the axial speed. As will be described in detail hereinafter, the subtraction of two consecutive echographic lines enables the removal of the fixed echoes and the reduction of the effects of the echoes corresponding to slow motions.

The invention will be described in detail hereinafter with reference to the accompanying diagrammatic drawing.

Figure 1:
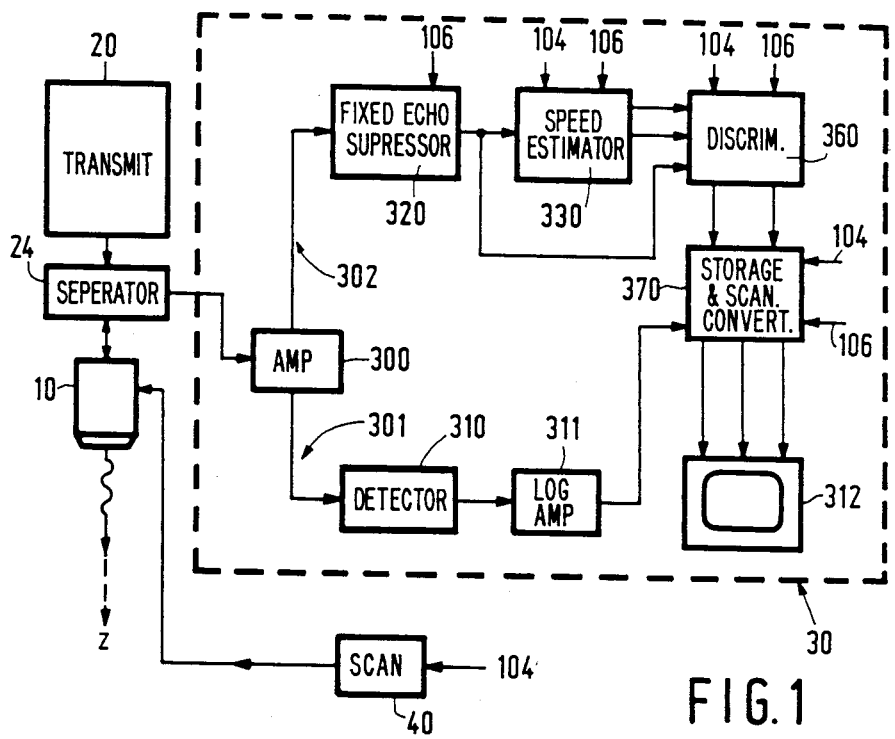
FIG. 1 shows an embodiment of a device in accordance with the invention.

FIG. 1 shows a diagram of a device for examining a moving object by means of ultrasound echography, enabling the measurement of the axial speed of said motion, i.e. the projection of the speed on the axis "z" of a beam of ultrasound excitations periodically transmitted by an ultrasound transducer 10 with a repetition period "T". The device also comprises a transmission stage 20, a stage 30 for receiving and processing echographic signals returned to the transducer 10, as well as a device 40 for mechanical scanning control of the transducer. Instead of this transducer, however, an array of transducers could be used which are then associated with an electronic scanning control device.

Figure 2:
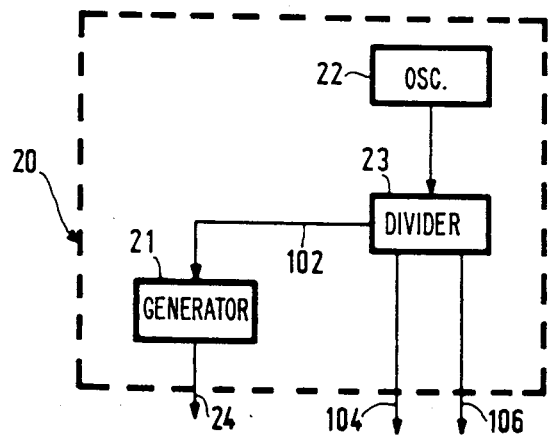
FIG. 2 shows a specific embodiment of the transmission stage of the device shown in FIG. 1.

In the embodiment which is shown in greater detail in FIG. 2, the transmission stage 20 comprises a generator 21 for electric excitation signals which are applied to the transducer 10 which converts these signals into trains of periodic pulsed ultrasound signals. This transmission is controlled by clock signals which are present on a connection 102 and which are supplied with a repetition frequency "F" (for example in the order of magnitude of 5 kHz) which is determined by a sequencer which successively comprises an oscillator 22, (in this case having a frequency of 32 MHz), and a frequency divider 23. The divider supplies the clock signals on the connection 102 as well as other control signals on the connections 104 and 106 with a frequency of 1 kHz and 16 MHz, respectively, in the present example. The control signals on the connection 104 control notably the device 40 for the scanning of the transducer. A separator 24 between the transducer stage 20 and the receiving and processing stage 30 is inserted between the transducer 10 and said stages 20, 30 so that the receiving circuits cannot be overloaded by the transmitted signals.

The receiving and processing stage 30 comprises, connected to the output of the separator 24, a high-frequency amplifier 300 with gain compensation as a function of depth, followed by two processing channels 301 and 302 which are connected in parallel. The channel 301 is of a conventional type and in this case comprises a series connection of an enveloped detector 310, a logarithmic compression amplifier 311, a storage and scan conversion device 370 enables the formation of grey scale images of cross-sections of the objects examined according to the principle of conventional echography.

As appears from FIG. 1, the second channel 302 of said receiving and processing stage 30 for the echographic signals comprises a circuit 330 for estimating the axial speed which enables, on the basis of a time analysis of the signal, the time shift $\tau_i(t)$ induced by the motion of the object between two successive echoes $e_i(t)$ and $e_{i+1}(t)$ to be extracted by means of a limited development of the relation (1):

$$e_{i+1}(t) = e_i[t - \tau_i(t)]$$

linking the two echoes, or $$e_{i+1}(t) = \sum_{n=0}^{p} \frac{(-1)^n}{n!} e_1^{(n)}(t) \cdot \tau_i^{n}(t) \quad (3)$$

where $e_{i+1}(t)$ can be measured directly and the derivatives $e_i^{(n)}(t)$ can be electronically calculated. The relation (3) represents an equation in $\tau_i(t)$ which need only be solved in order to extract the desired time shift $\tau_i(t)$. The axial speed $V_{iz}(t)$ is derived therefrom by applying the following formule:

$$V_{iz}(t) = \tau_i(t) C/2T \quad (5)$$

where C represents the propagation speed of the ultrasound wave.

Figure 3:
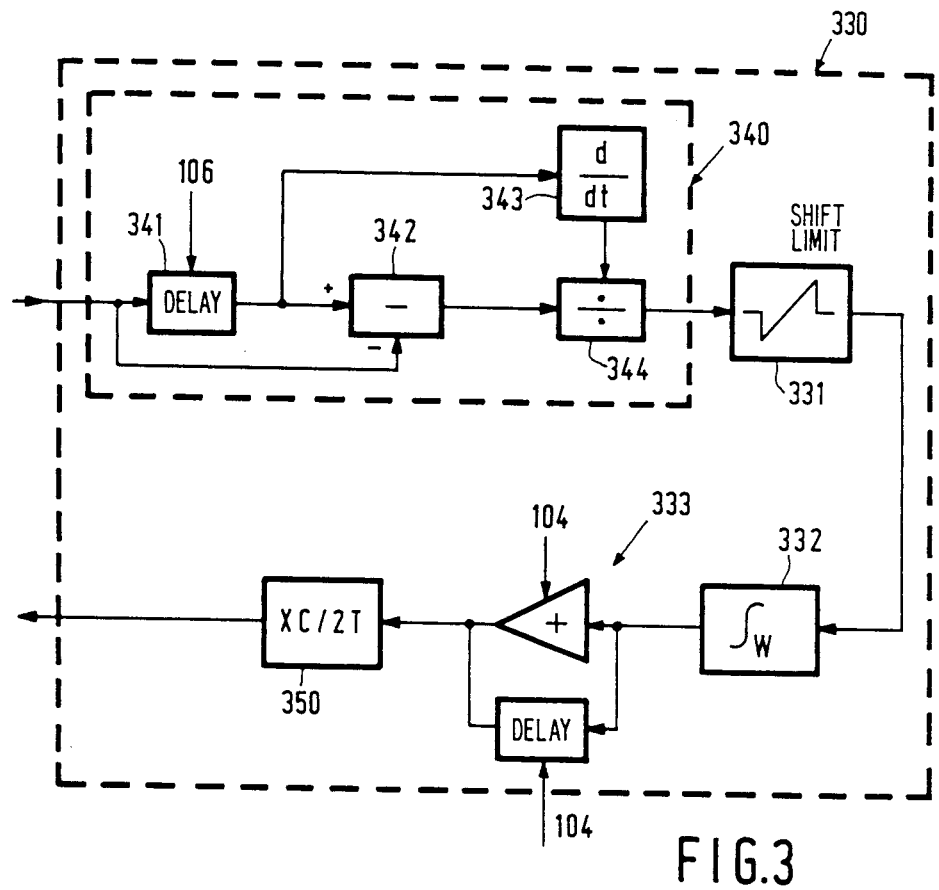
FIG. 3 shows a preferred embodiment of a circuit for estimating the axial speed.

Therefore, in accordance with FIG. 3, the circuit 330 for estimating the axial speed comprises on the one hand a circuit 340 for extracting the time shift $\tau_i(t)$ which is constructed so as to solve the equation (3) and on the other hand a circuit 350 for multiplication by $C/2T$.

In practice the time shift $\tau_i(t)$ is very small with respect to the characteristic variation times of the echographic signal. For example, application of the formula (2) with $T=200$ μs, $C=1500$ m/s and $V_{iz}(t)=5$ cm/s (blood flows, movements of the heart walls) leads to: $\tau_i(t)=13.3$ ms.

For an echographic signal which is centred around 4 MHz, the time shift is effectively smaller than one tenth of the period of the signal, so 250 ns. Consequently, a development limited to the first order of the relation (1) is justified. With $n=1$, the equation (3) is then written as:

$$e_{i+1}(t)=e_i(t)-e_i^{(1)}(t)\tau_i(t) \quad (6)$$

or $$\tau_i(t)=[e_i(t)-e_{i+1}(t)]/e_i^{(1)}(t) \quad (4)$$

The circuit 340 for extracting the time shift as shown in FIG. 3 is a completely analog embodiment for calculating the expression (6). To this end, the circuit 340 is composed of a delay line 341, a subtractor 342, a circuit 343 for calculating the first derivative with respect to time, and a divider 344. A delay line having the required qualities, i.e. long delay (200 μs), high stability (250 ps), a wide dynamic range (79 dB) and a large passband (4 MHz), is described in French Pat. 2 415 391.

However, its digital implementation is also conceivable. The calculation of the derivative, however, requires a few precautions. Actually, when the echographic signal is sampled in the step $\Delta T$ of the signal 106 (60 ns in the described example), the points obtained are situated too far from one another for obtaining a satisfactory estimation of the derivative of means of the relation:

$$e_i^{(1)}(k\Delta T)=[e_i((k+1)\Delta T)-e_i(k\Delta T)]/\Delta T.$$

The solution is to shift, in an analog manner, the echo $e_i(k\Delta T)$ by a period "$\epsilon$" which is small with respect to $\Delta T$ ($\epsilon=5$ ns, for example), followed by subtracting $e_i(k\Delta T-\epsilon)$ from $e_i k\Delta T$ and, finally, by dividing the difference obtained by $\epsilon$, in accordance with the formule:

$$e_i^{(1)}(k\Delta T)=[e_i(k\Delta T)-e_i(k\Delta T-\epsilon)]/\epsilon.$$

In order to reduce the estimation noise, it is advantageous to practice to place the mean value of the time shift $\tau_i(t)$, calculated by the general relation (3) and notably by the relation (4), on a time window having a width $W$ in order to evaluate a mean time shift $\overline{\tau}_i(t)$ which is defined by:

$$\overline{\tau}_i(t) = \frac{1}{W} \int_t^{t+W} \tau_i(u)\,du.$$

This operation is performed by an integrator/averaging circuit 332 which is connected between the circuit 340 for extracting the time shift and the circuit 350 for multiplication by $C/2T$. Thus, a corresponding mean axial speed $\overline{V}_{iz}(t)$ is deduced as follows:

$$\overline{V}_{iz}(t)=\overline{\tau}_i(t)C/2T.$$

After calculation of $\overline{\tau}_i(t)$ and before multiplication by $C/2T$, a mean value of $\tau_i(t)$ can also be formed for N consecutive excitations at a rhythm which is given by the signal 104; in this case this results in a mean value over $N=5$ excitations. This mean value is formed by the circuit 333 shown in FIG. 3; thus on the output of this circuit there is obtained:

$$\overline{\tau}(t) = \frac{1}{N} \sum_{k=1}^{N} \tau_k(t)$$

so that the axial speed is:

$$\overline{V}_z(t)=\overline{\tau}(t)C/2T.$$

Figure 5:
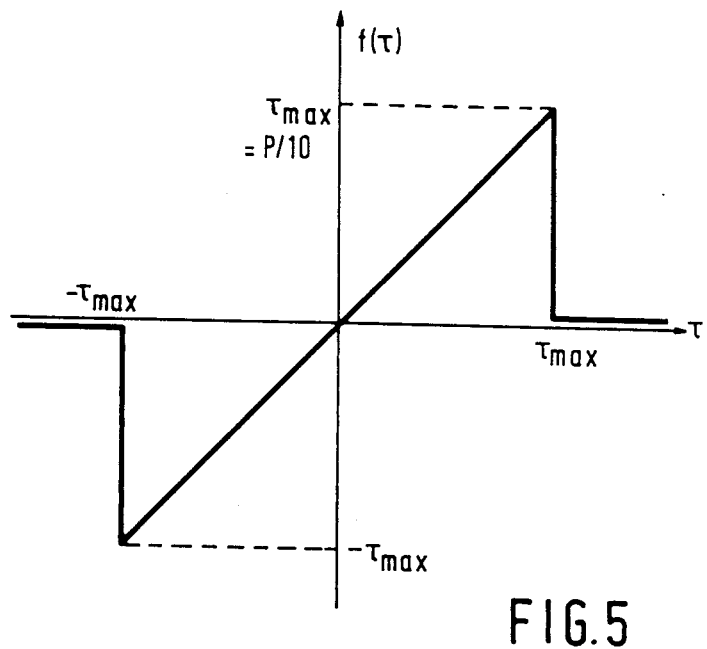
FIG. 5 shows a diagram giving a law for limiting the time shift values $\tau_i(t)$.

However, in order to remain within the validity range of the limited development defined by the relation (6) which assumes $\tau_i(t)$ to be sufficiently small, it is advantageous to limit the values of $\tau_i(t)$, represented by a distribution function $f(\tau)$ which is anulled when the absolute value of $\tau$ exceeds a maximum value $\tau_{max}$. FIG. 5 shows an example of such a distribution function: when $\tau$ is between $-\tau_{max}$ and $\tau_{max}$, $f(\tau)=\tau$, and when $|\tau|>\tau_{max}$, $f(\tau)=0$. $\tau_{max}$ may be taken to equal one tenth of the period P of the echographic signal, so 25 ns for $P=250$ ns. In that case the mean time shift $\overline{\tau}_i(t)$ is given by:

$$\overline{\tau}_i(t) = \frac{1}{W} \int_t^{t+W} f[\tau_i(u)]\,du.$$

To this end, the circuit 330 for estimating the axial speed comprises a circuit 331 for limiting the time shift values which is situated between the circuit 340 for extracting the time shift and the integrator/averaging circuit 332.

Figure 6:
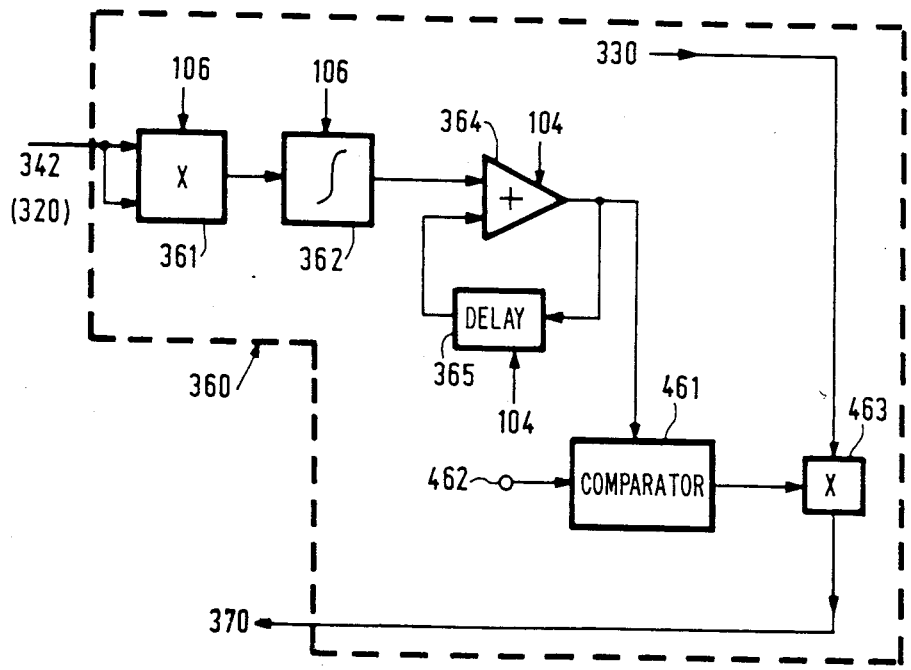
FIG. 6 shows a discriminator circuit of the device shown in FIG. 1.

The output signal of the circuit 330 for estimating the axial speed is thus validated or not by a discriminator circuit 360 as shown in FIG. 6, after which the values thus confirmed are applied to the display device 312 via the colour encoding device 370.

The presence of the discriminator circuit 360 is indispensable. Actually, if the successive echographic lines obtained in the rhythm of the excitations initiated by the signal 102 at the frequency $F=1/T$ are supplied by perfectly fixed targets, the result of the difference between these two lines will only be noise. Generally speaking, an echographic line can be described as follows:

$$y_i(t)=q(t)+e_i(t)$$

where $q(t)$ is the signal caused by fixed targets and $e_i(t)$ is the echo produced by the moving object.

The difference $d_i(t)$ between two consecutive lines thus amounts to:

$$d_i(t)=y_{i+1}(t)-y_i(t)=e_{i+1}(t)-e_i(t) \quad (7)$$

If the echographic lines $y_i(t)$ originate only from fixed targets during a given time interval, it appears from (7) that $d_i(t)=0$ except for noise. Thus, the result supplied by the circuit 330 for estimating the axial speed which processes this noise does not include a speed zero, so that it is necessary to validate this result or not. To this end, the circuit 360 comprises, connected in series, a multiplier 361 which receives the output signal $d_i(t)$ of the subtractor 342 on both its inputs and which squares the difference signal. An integrator 362 enables calculation of the local energy on a window having a width $W'$ (possibly equal to $W$) in accordance with the formule:

$$E_i(t) = \int_t^{t+W} d_i^2(u)du.$$

A circuit 364, 365 for calculating the mean value is formed, as in the case of the circuit 333, by an accumulator which comprises an adder 364 and a delay line 365 which introduces a delay T (or a multiple of T), and enables the formation of the mean value of the local energy over M activations, that is to say (M−1) differences in accordance with the expression:

$$E(t) = \frac{1}{M-1} \sum_{i=1}^{i=M-1} E_i(t) \quad (12)$$

The value thus obtained is applied to a validation circuit which comprises a comparator 461 which receives on a first input the ouput signal of the accumulator 364, 365 (or directly that of the summing device 362 in the case where the circuit for calculating the mean value is not provided) and on a second output 462 a reference voltage which forms a threshold. The output signal of the comparator is logic 0 or 1, depending on whether the voltage received on its first input is lower than or higher than, respectively, the refence threshold $\Delta N(t)$ which is proportional to the level of the noise $N(t)$. A multiplier 463, a first input of which receives the output signal $\overline{V}_z(t)$ of the circuit 330, applies this signal, denoted hereinafter as $\overline{V}'_z(t)$ on an output or simply supplies the values zero, depending on whether the validation signal applied to a second input by the comparator 461 is 1 or 0, respectively. Actually, outside the true flow zones the mean energy calculated on the output of the circuit 364, 365 is that of noise only, and can in principle be measured alone, in the absence of excitation, in order to determine the appropriate threshold value; thus, $N(t)$ is also given by:

$$\int_t^{t+W} d_i^2(u)du$$

outside any excitation. The effective threshold level is thus determined by the coefficient $\alpha$ to be chosen by the operator. However, in the presence of signals returned by the moving targets, the mean energy of the signal $d_i(t)$ exceeds that of the noise alone, thus authorizing the validation of the signals supplied by the circuit 330 for estimating the axial speed.

It is to be noted that the value of $\alpha$ can also be used for the display in order to establish a limit between colour display and display in grey; if $E(t)$ exceeds the threshold $\alpha N(t)$, the display will be in colour. However, it will be grey if $E(t)$ is below the threshold.

The output circuit of the discriminator circuit 360 is applied to the device for storage, scan conversion and colour encoding 370 which also receives, prior to display, the output signal of the amplifier 311 of the processing channel 301. A device of this kind is described, for example in European Patent Application EP-A 0 100 094. FIG. 3 of this document actually shows, connected between the terminals A, B, C and $E_R$, $E_G$, $E_B$, an example of the circuits which can be used, the terminal A receiving the conventional echographic signal and the terminals B and C receiving the parameters which are characteristic of the moving device 312 thus enable real-time display of flows or displacements superposed on the conventional echographic reflection image.

Figure 4:
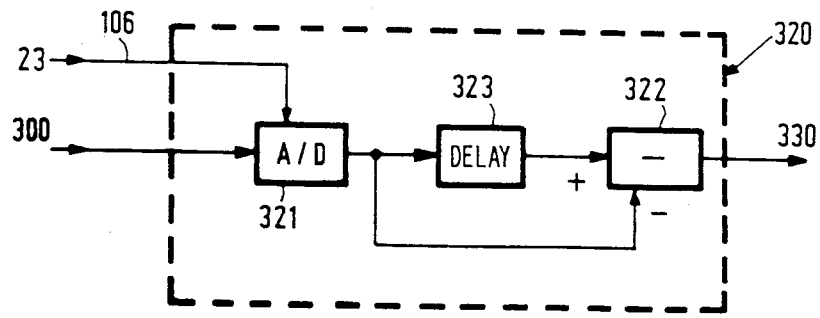
FIG. 4 shows a circuit diagram of a circuit for suppressing the fixed echoes and for attenuating the echoes relating to slow motions.

FIG. 4 shows the diagram of a circuit 320 for suppressing the fixed echoes and for attenuating the echoes relating to slow movements, which is particularly necessary in the case of examination of blood flows.

The digital circuit 320 for suppressing the echoes as shown in FIG. 4 itself comprises, in the present embodiment, an analog-to-digital converter 321 whose output is connected on the one hand directly to the negative input of a subtractor 322 and on the other hand to the positive input of this subtractor via a delay circuit 323. The delay introduced by the circuit 323 could amount to several periods $T = 1/F$, but is preferably chosen to be as small as possible and equal to T.

The subtractor 322 thus forms the difference $d_i(t)$ between two successive echographic lines $y_i(t)$ and $y_{i+1}(t)$. Therefore, if the circuit 320 is present, its output can be connected directly to the input of discriminator circuit 360 which also requires $d_i(t)$ to be known. On the other hand, because the repetition relation $$e_{i+1}(t) = e_i[t - \tau_i(t)]$$

is also verified by $d_i(t)$, the output signal of the circuit 320 serves as an input signal for the circuit 330 for estimating the axial speed.

The circuit 320 is provided for the elimination of all fixed echoes, notably those whose occurrence is caused by reflection of the ultrasound waves from the walls of vessels where the flows being studied occur. The presence of fixed echoes is distrubing because their amplitude (in the order of +40 dB in the case of blood flows) is much higher than that of the useful signals, that is to say the signals returned by the moving targets. The circuit 320 is also controlled, via the connection 106, by the frequency divider 23 of the sequence which supplies this circuit with the sampling control signal having a frequency of 16 MHZ.

What is claimed is:
1. Apparatus for examining a moving object which has a velocity of means of ultrasound echography to enable the measurement of a projection of the velocity of said object on an axis of a beam of ultrasound pulses which propagate toward the object with a propagation velocity, C, comprising:

means which periodically transmit said ultrasound pulses toward the object using a repetition period, T; and means which receive and process echographic signals which include a plurality of echoes of said pulses which are returned to the apparatus from the object wherein as an improvement said means which receive and process include:

a circuit (330) for estimating said projection of the velocity, $v_{iz}(t)$, which circuit comprises:

first calculating means (340) for producing an output corresponding to a time shift, $\tau_i(t)$, between two successive echoes $e_i(t)$ and $e_{i+1}(t)$ in said echographic signal which function to solve for $\tau_i(t)$ the equation:

$$e_{i+1}(t) = \sum_{n=0}^{p} \frac{(-1)^n}{n!} e_i^{(n)}(t) \cdot \tau_i^n(t)$$

where $e_i^{(n)}(t)$ is a derivative of order n with respect to time of the echo $e_i(t)$ and second calculating means (350) connected to multiply the output of the first calculating means for C/2T in order to produce an output representing $V_{iz}(t)$.

2. Apparatus as claimed in claim 1 wherein the first calculating means comprise a delay line (341) connected to receive said echoes at an input; a subtractor connected to subtract said echoes from an output of said delay line; means for calculating the derivative of said output to said delay line; and divider means connected to receive an output of said means for calculating the derivative and for dividing said output by an output of said subtractor.

3. Apparatus as claimed in claim 2 wherein said circuit for estimating further comprises an integrator/averaging circuit (332) connected in cascade between the output of the first calculating means and an input of the second calculating means.

4. Apparatus as claimed in claim 3 further comprising means for limiting time shift values $\tau_i(t)$ connected to cascade between the output of the divider means and an input of the integrator/averaging circuit.

5. The apparatus of any one of claims 1, 2, 3 or 4 further comprising a discriminator circuit connected to process the output of said second calculating means, said discriminator circuit comprising:
means for squaring the difference $d_i(t)$ between two successive echoes;
summing means which act on a window having a width W' which calculates a value $$\overline{E}(t) = \int_t^{t+W'} d_i^2(u)\, du;\text{ and}$$

validation circuit means which compare E(t) with a threshold, said threshold being proportional to a noise level.

6. The apparatus of claim 12 further comprising means for eliminating echoes attributable to objects which are fixed or are moving slower than the moving object which is being examined before said echoes are applied to an input of said circuit for estimating said axial velocity.

7. The apparatus of claim 1, 2, 3, or 4 further comprising means for eliminating echoes attributable to objects which are fixed or are moving slower than the moving object which is being examined before said echoes are applied to an input of said circuit for estimating said axial velocity.

8. A method for examining moving objects by means of ultrasound echography comprising the steps of:
directing pulses of ultrasound energy which propagate with a velocity C towards said moving object;
receiving echoes of said ultrasound energy from said object and producing electrical signals characteristic thereof;
processing said electrical signals to extract a time shift $\tau_i(t)$ between two successive echoes $E_i(t)$ and $E_{i+1}(t)$ to solve for $\tau_i(t)$ the equation $$e_{i+1}(t) = \sum_{n=0}^{p} \frac{(-1)^n}{n!} e_i^{(n)}(t) \cdot \tau_i^n(t)$$

where $e_i^{(n)}(t)$ is a derivative of order n with respect to time of the echo $e_i(t)$; and
calculating said axial velocity by multplying said value of $\tau_i(t)$ by C/2T.

9. The method of claim 8 further comprising the step of rejecting from said calculation of $\tau_i(t)$ echoes which originate from objects which are fixed or are moving slower than the moving objects which are being examined.

* * * * *